(12) United States Patent
Cros et al.

(10) Patent No.: US 6,737,235 B1
(45) Date of Patent: May 18, 2004

(54) NUCLEIC ACID ISOLATION

(75) Inventors: Philippe Cros, Lyons (FR); Abdelhamid Elaissari, Lyons (FR); Claude Mabilat, Rillieux la Pape (FR); Christian Pichot, Corbas (FR); Marc Rodrigue, Dardilly (FR); Lise Santoro, Sainte-Foy-les-Lyons (FR)

(73) Assignee: Bio Merieux, Marcy l'Etoille (FR)

( * ) Notice: Subject to any disclaimer, the term of this patent is extended or adjusted under 35 U.S.C. 154(b) by 532 days.

(21) Appl. No.: 08/945,731

(22) PCT Filed: Mar. 20, 1997

(86) PCT No.: PCT/FR97/00496

§ 371 (c)(1),
(2), (4) Date: Nov. 10, 1997

(87) PCT Pub. No.: WO97/34909

PCT Pub. Date: Sep. 25, 1997

(30) Foreign Application Priority Data

Mar. 20, 1996 (FR) .............................. 96 03753
Apr. 9, 1996 (FR) .............................. 96 04691

(51) Int. Cl.$^7$ ...................... C07H 21/04; C12N 15/11; C12Q 1/68
(52) U.S. Cl. ......................... 435/6; 536/23.1
(58) Field of Search .............................. 435/6; 536/23.1

(56) References Cited

U.S. PATENT DOCUMENTS

| 4,767,700 A | 8/1988 | Wallace | 435/6 |
| 4,912,032 A | * 3/1990 | Hoffman et al. | 435/7 |
| 4,997,932 A | 3/1991 | Reardon et al. | 536/25.4 |

(List continued on next page.)

FOREIGN PATENT DOCUMENTS

| DE | 37 17 209 A | 12/1988 |
| EP | 0 161 881 A | 11/1985 |
| EP | 0 366 241 A | 5/1990 |

(List continued on next page.)

OTHER PUBLICATIONS

F. Meunier et al., "Preparation and charaterization of cationic poly (n–isopropylacrylamide) copolymer latexes".
D. Treco, "Preparation of Genomic DNA: Phenol Extraction and Concentration of DNA from Aqueous Solutions", *Short Protocols in Molecular Biology*, $2^{nd}$ Ed., Harvard Medical School, 1992, pp. 2–4 through 2–7.

(List continued on next page.)

*Primary Examiner*—Remy Yucel
*Assistant Examiner*—Nancy Vogel
(74) *Attorney, Agent, or Firm*—Oliff & Berridge, PLC

(57) ABSTRACT

A method for aqueous phase nucleic acid isolation from a sample, comprising a step of nucleic acid adsorption on a particulate substrate, is disclosed. The method comprises an adsorption reagent preparation step (a) that includes a sol consisting of a aqueous continuous phase and a dispersed particulate substrate phase including a functionalized particulate polymer prepared by polymerizing (1) a first water-soluble acrylamide or acrylamide derivative monomer, (2) at least one cross-linking agent and (3) at least one second water-soluble, cationic and functional monomer, said polymer having a predetermined lower critical solubility temperature (LCST) of 25–45° C.; a contact step (b) wherein the adsorption reagent is contacted with the sample containing the nucleic acid; an adsorption step (c) wherein, to carry out the contact step (b), at least one parameter is selected for the reaction medium, said parameters being a pH no higher than 7, an ionic strength no higher than $10^{-2}$ M, and a temperature lower than the polymer LCST; a separation step (d) wherein the dispersed phase is separated from the continuous phase, optionally after it has been observed that adsorption has occurred; and a desorption step (e) wherein the nucleic acid is desorbed from the particulate substrate by increasing the ionic strength until an ionic strength higher than $10^{-2}$ M is achieved.

22 Claims, 4 Drawing Sheets

U.S. PATENT DOCUMENTS

Figure 1:
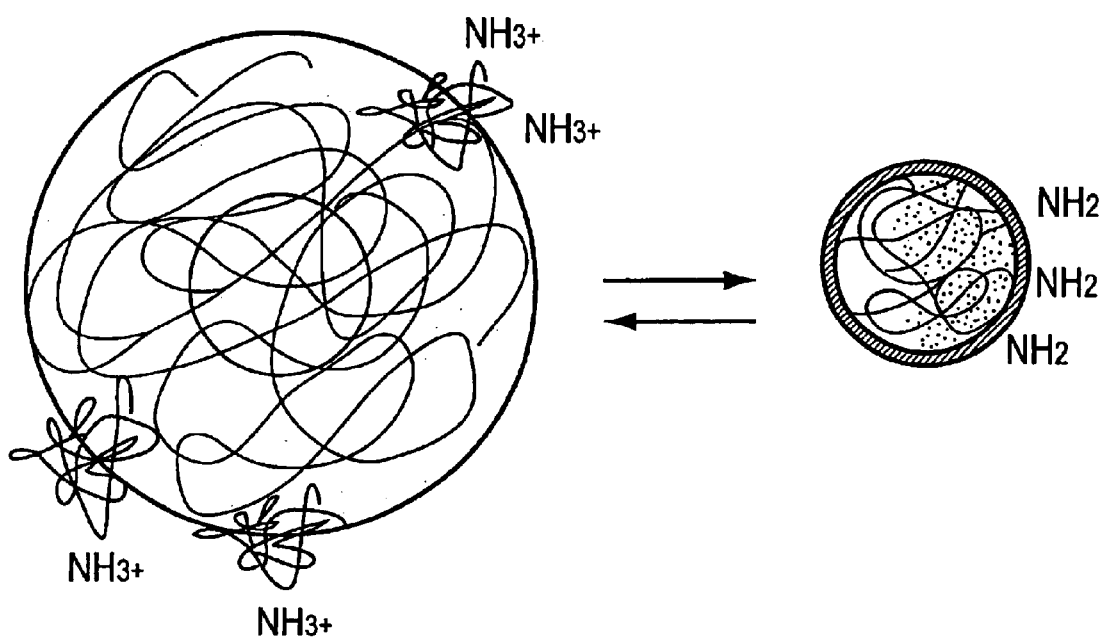

| | | | | |
|---|---|---|---|---|
| 5,122,600 | A | * 6/1992 | Kawaguchi et al. | 536/27 |
| 5,206,136 | A | * 4/1993 | Monji et al. | 435/5 |
| 5,225,062 | A | * 7/1993 | Yoshioka et al. | 204/299 |
| 5,280,076 | A | * 1/1994 | Sasaki et al. | 525/310 |
| 5,434,270 | A | * 7/1995 | Ponticello et al. | 548/338.1 |
| 5,508,164 | A | * 4/1996 | Kausch et al. | 435/6 |
| 5,569,364 | A | * 10/1996 | Hooper et al. | 204/455 |

FOREIGN PATENT DOCUMENTS

| | | | |
|---|---|---|---|
| EP | 0 501 301 A | 9/1992 | |
| WO | 161881 | * 11/1985 | 526/307.4 |
| WO | WO A 95/04140 | 2/1995 | |

OTHER PUBLICATIONS

F. Mallet et al., "Enzyme–Linked Oligosorbent Assay for Detection of Polymerase chain Reaction–Amplified Human Immunodefiency Virus Type 1", *Journal of Clinical Microbiology*, vol. 31, No. 6, Jun. 1993, pp. 1444–1449.

H. Inomata et al., "Measurement and Correlation of the Swelling Pressure of N–Isopropylacrylamide Gel". *Macromolecules*. vol. 27, 1994, pp. 6459–6464.

M. Goodman. "DNA Polymerase Fidelity: Misinsertions and Mismatched Extensions". *PCR Strategies*. Academic Press, 1995, pp. 17–31.

C. Mabilat et al., "Routine Identification of *Mycobacterium tuberculosis* Complex Isolates by Automated Hybridization", *Journal of Clinical Microbiology*, Nov. 1994, p. 2702–2705.

T. Kievits. "NASBA Isothermal Enzymatic In Vitro Nucleic Acid Amplicication Optimized for the Diagnosis of HIV–1 Infection". *Journal of Virological Methods*, vol. 35, 1991, pp. 273–286.

D. Voytas, "Resolution and Recovery of Large DNA Fragments: Agarose Gel Electrophoresis". *Short Protocols in Molecular Biology*, $2^{nd}$ Ed., Harvard Medical School, 1992, pp. 2–13 through 2–14.

G. Arora, "Characterization of Enzyme Profiles of *Lactobacillus casei* Species by a Rapid API ZYM System", *Journal of Dairy Science*, vol. 73, No. 2, 1990, pp. 264–273.

* cited by examiner

NUCLEIC ACID ISOLATION

The present invention belongs to the field of purification of nucleic acids, in aqueous medium.

A process is known according to the document WO-A-95/04140 for purifying, in aqueous medium, nucleic acids present in a sample, according to which said sample is brought into contact with a particulate system consisting of silica beads, in the presence of a chaotropic substance, and then the nucleic acids attached to the beads are separated from the final aqueous solution.

In accordance with the document F. Meunier et al., Polymers for Advanced Technologies, Volume 6, pp. 489–496, (1995), the preparation of a polymer called PNIPAM, by polymerization of (1) N-isopropylacrylamide, (2) N,N-methylenebisacrylamide and (3) 2-aminoethylmethacrylate chloride, in the presence of a polymerization initiator, is described. The behavior of this surface-functionalized polymer can make it particularly suited to a covalent attachment of biological molecules.

The document EP-A-0 161 881 teaches that a heat-sensitive polymer such as the polymers obtained by copolymerization of monomers of N-alkyl- or of N-alkylene-acrylamide or methacrylamide and of monomers of acrylic or methacrylic derivatives, can be used in the isolation of biological material, by virtue of its capacity to change structure as a function of the temperature. It has an open structure at low temperature, which facilitates the attachment of a biological material, and a retracted structure at high temperature, which allows the liberation of the attached biological material. The control of the steps of attachment and liberation of the biological material can therefore be performed by varying the temperature. For a better control, it is possible, in addition, to vary the pH.

The use proposed by this document extends to the isolation of any biological material present in a sample, and in particular nucleic material and protein material, without any specificity.

According to the invention, a process for the selective isolation of a nucleic material present in a sample is provided. Even if the sample is complex and contains a protein material and/or inhibitors of enzymatic reaction, the process of the invention limits or even eliminates any isolation of the protein material and/or of said inhibitors, while promoting the isolation of the nucleic material.

A process for the isolation in aqueous phase, according to the invention, of a nucleic material present in a sample, comprises the following steps:

according to a so-called step (a) for producing the adsorption reagent, an adsorption reagent is available which comprises a sol consisting of an aqueous continuous phase and a discontinuous phase of the particulate support which comprises a functionalized, particulate polymer, said polymer being obtained by polymerization of (1) a first water-soluble monomer of acrylamide or of an acrylamide derivative, (2) at least one cross-linking agent and (3) at least a second cationic and water-soluble functional monomer, said polymer having a predetermined lower critical solubility temperature (LCST) which is between 25 and 45° C., preferably between 30 and 40° C., according to a so-called step (b) for bringing into contact, the adsorption reagent is brought into contact with the sample containing the nucleic material, according to a so-called adsorption step (c), for the bringing into contact according to (b), at least one and preferably at least two of the following parameters for the reaction medium are chosen:

pH at most equal to 7, ionic strength at most equal to $10^{-2}$ M, temperature less than the LCST of the polymer, according to a so-called separation step (d), after having optionally observed that the adsorption has taken place, the discontinuous phase and in particular that having adsorbed the nucleic material are separated from the continuous phase, according to a so-called desorption step (e), the nucleic material is dissociated, by desorption, from the particulate support by increasing the ionic strength up to an ionic strength greater than $10^{-2}$ M.

Advantageously, for the desorption step (e), at least one of the parameters selected from the pH and the temperature is in addition varied as follows:

increase in the pH up to a pH greater than 7, increase in the temperature up to a temperature greater than the LCST of the polymer.

The invention also relates to a process for the isolation, in aqueous phase, of a nucleic material present in a sample, comprising a step of adsorption of said nucleic material, onto a particulate support, allowing a use as such of the nucleic material adsorbed onto the particulate support, in a subsequent analytical step. This process comprises the following steps:

according to a so-called step (a) for producing the adsorption reagent, an adsorption reagent is available which comprises a sol consisting of an aqueous continuous phase and a discontinuous phase of the particulate support which comprises a functionalized, particulate polymer, said polymer being obtained by polymerization of (1) a first water-soluble monomer of acrylamide or of an acrylamide derivative, (2) at least one cross-linking agent and (3) at least a second cationic and water-soluble functional monomer, and said polymer having a predetermined lower critical solubility temperature (LCST) which is between 25 and 45° C., according to a so-called step (b) for bringing into contact, the adsorption reagent is brought into contact with the sample containing the nucleic material, according to a so-called adsorption step (c), for the bringing into contact according to (b), an ionic strength at most equal to $10^{-2}$ M is selected for the reaction medium, according to a so-called separation step (d), after having optionally observed that the adsorption has taken place, the discontinuous phase is separated from the continuous phase, according to which process the desorption step is optional.

In accordance with a preferred embodiment of the latter process, according to the adsorption step (c), for the bringing into contact according to (b), at least one of the following parameters is in addition selected for the reaction medium:

pH at most equal to 7, temperature less than the LCST of the polymer.

Of course, this process may comprise, after the separation step (d), a so-called desorption step according to which the nucleic material is dissociated, by desorption, from the particulate support by varying at least one of the parameters selected from the ionic strength, the pH and the temperature, as follows, increase in the ionic strength up to an ionic strength greater than $10^{-2}$ M increase in the pH up to a pH greater than 7, increase in the temperature up to a temperature greater than the LCST of the polymer.

At least the ionic strength is advantageously varied.

The processes defined above according to the invention will be preferably carried out according to two variants related to step (a).

According to a first variant which will be illustrated in the examples, the particulate support consists of said particulate polymer, and in this case, the cross-linking agent(s) (2) are water-soluble.

According to a second variant, the particulate support comprises, in addition, an organic or inorganic core, completely or partially coated with said particulate polymer, said core not modifying the adsorption properties of the polymer in relation to said nucleic material. The core or core portion then fulfills the function of the cross-linking agent (2), it being possible to provide another cross-linking agent of the water-soluble cross-linking agent type. By way of example, the core may be a polystyrene core, and/or comprise a magnetic compound.

According to a specific and preferred embodiment of these processes, at least one probe and/or one primer capable of specifically hybridizing to the nucleic material before or after step (b) is added to the sample before step (b), or to the reaction medium after step (b), and in particular after step (c) or step (d).

In another specific embodiment, the nucleic material consists of a probe or a primer, and according to (b) and (c), the adsorption reagent is brought into contact with said nucleic material in order to obtain a hybridization reagent, and then according to (b'), after having optionally observed that the adsorption has taken place, and separated the hybridization reagent from the reaction medium, said hybridization reagent is brought into contact with a medium containing at least one nucleic acid or nucleic acid fragment, under suitable conditions for the hybridization or the extension of the primer.

The particulate polymer is advantageously obtained by free radical polymerization in the presence of a cationic or neutral, and water-soluble, polymerization initiator.

The first monomer (1) is preferably selected from the N-alkylacrylamides and the N,N-dialkylacrylamides, and more particularly from N-isopropylacrylamide, N-ethylmethacrylamide, N-n-propylacrylamide, N-n-propylmethacrylamide, N-isopropylmethacrylamide, N-cyclopropylacrylamide, N,N-diethylacrylamide, N-methyl-N-isopropylacrylamide, N-methyl-N-n-propylacrylamide, the first monomer being preferably N-isopropylacrylamide (NIPAM).

The second functional monomer(s) (3) are preferably selected from the acrylic and methacrylic derivatives, 2-aminoethylmethacrylate chloride (AEM), the N-vinylpyridine derivatives, the trialkylammonium derivatives and the isothiouronium chloride derivatives.

Advantageously, the water-soluble cross-linking agent (2) is selected from N,N-methylenebisacrylamide (MBA), ethylene glycol dimethacrylate, and the polymerization initiator is 2,2'-azobisamidinopropane chloride (V50).

The separation step (d) is preferably carried out according to a technique selected from centrifugation, filtration, precipitation, sedimentation and the application of a magnetic field.

Before the separation step (d), it can be optionally observed that the adsorption reaction has occurred. By way of example, HPLC or capillary electrophoresis techniques may be used.

Before disclosing the invention in greater detail, some terms used in the present description and in the claims are defined below:

isolation of a nucleic material according to the invention is understood to mean the separation, detection of this material, the enrichment of a fraction with nucleic material, according to a specific or a specific method of isolation, in a qualitative and/or quantitative manner.

A nucleic material according to the invention is a nucleic acid, a nucleic acid fragment, a mixture of nucleic acids and/or of nucleic acid fragments, or a fraction of nucleic acids and/or of fragments of nucleic acids. Nucleic acid is understood to mean any nucleic acid, in a free form or optionally combined with proteins, regardless of its cellular, bacterial or viral origin or the like. It is either a deoxyribonucleic acid or ribonucleic acid, consisting of a stretch of natural nucleotides whose constituent elements are a sugar, a phosphate group and a nitrogen base selected from adenine, guanine, uracil, cytosine, thymine and/or of nucleotides modified in at least one of the three constituent elements; by way of example, the modification may take place at the level of the bases, generating modified bases, such as inosine, 5-methyldeoxycytidine, deoxyuridine, 5-dimethylaminodeoxyuridine, 2,6-diaminopurine, 5-bromodeoxyuridine, and such as bases modified by a tracer detectable directly or indirectly by techniques known to persons skilled in the art, by way of example bases modified by biotin; at the level of the sugar, namely the replacement of at least one deoxyribose by a polyamide; and/or at the level of the phosphate group, for example its replacement by esters selected in particular from the diphosphate, alkyl- and arylphosphonate and alkyl- and arylphosphorothioate esters. The nucleic acid according to the invention is completely or partially single-stranded and/or double-stranded, in particular it may consist of a probe-nucleic acid, probe-nucleic acid fragment, primer-nucleic acid or primer-nucleic acid fragment duplex; the duplex may be a homoduplex or a heteroduplex.

The invention is of course applied to the isolation of fragments of nucleic acids as defined above, or oligonucleotides (ODN), of variable sizes.

The nucleic material may be of natural origin, and/or obtained by genetic recombination and/or by chemical synthesis; by way of example, it may consist of a probe or a primer.

The present invention is applied to the aspecific isolation of a fraction of nucleic acids and/or of fragments of nucleic acids, which is contained in a sample, but also to the specific isolation of a nucleic acid or a nucleic acid fragment, or of a mixture of nucleic acids or of fragments of nucleic acids, which are present in a sample.

A sample as understood according to the invention comprises any sample capable of containing a nucleic material, in particular a biological sample such as that obtained from a biological fluid, a sample of food origin. The sample consists wholly or partly of a sample, in particular it may consist of an aliquot, a dilution. The sample may or may not have been subjected to a preliminary treatment, in particular of purification or lysis in order to facilitate the liberation of the nucleic acids.

The LCST of a polymer such as that which is the subject of the present invention is in particular defined and measured by techniques described in the following documents: Hiroshi Inomata et al., Macromolecules 1994, 27, 6459–6464.

A probe is a nucleotide fragment possessing a hybridization specificity under determined conditions for forming a hybridization complex with a nucleotide fragment. A probe used within the framework of the present invention will be preferably a capture probe, without nevertheless excluding the other types of probes from this context.

Primerr according to the invention is understood to mean a probe possessing a hybridization specificity under determined conditions for the initiation of an enzymatic polymerization, for example in an amplification technique such as PCR (Polymerase Chain Reaction), the so-called NASBA technique ("Nucleic Acid Sequence-Based Amplification") or alternatively the so-called TMA technique (Transcription Mediated Amplification), in an extension process, such as sequencing, in a reverse transcription method or the like.

Acrylamide derivative according to the invention is understood to mean a polymerizable monomer corresponding to the formula $R^0$—CH=C($R^1$)—CONR$^2R^3$, in which $R^0$, $R^1$, $R^2$ and $R^3$ represent a group selected independently from hydrogen, aliphatic or cyclic, linear or branched lower hydrocarbon groups, nitrogen-containing heterocyclic groups such as imidazole.

The adsorption of nucleic material as understood according to the present invention is defined as follows: a nucleic material is adsorbed onto a particulate support if, after a period of contact between said material and said support, at least one of the groups belonging to the constituent components of the nucleic material is attached to the surface of the support; the adsorption results from ionic interactions and/or hydrogen bonds, and possibly hydrophobic interactions, excluding any covalent bond, between the material and the support.

Finally, functionalized polymer is understood to mean a polymer having at least one interface carrying functional groups capable of generating with groups of the constituent components of the nucleic material any one of the interactions and/or bonds involved in the adsorption phenomenon. Preferably, these functional groups are selected from $NH_3^+$; $NH_4^+$; $NR_3^+$ or R represents an aliphatic or cyclic, saturated or unsaturated hydrocarbon group, it being possible for $NR_3^+$ to represent the pyridinium group; and the isothiouronium group.

Figure 2:
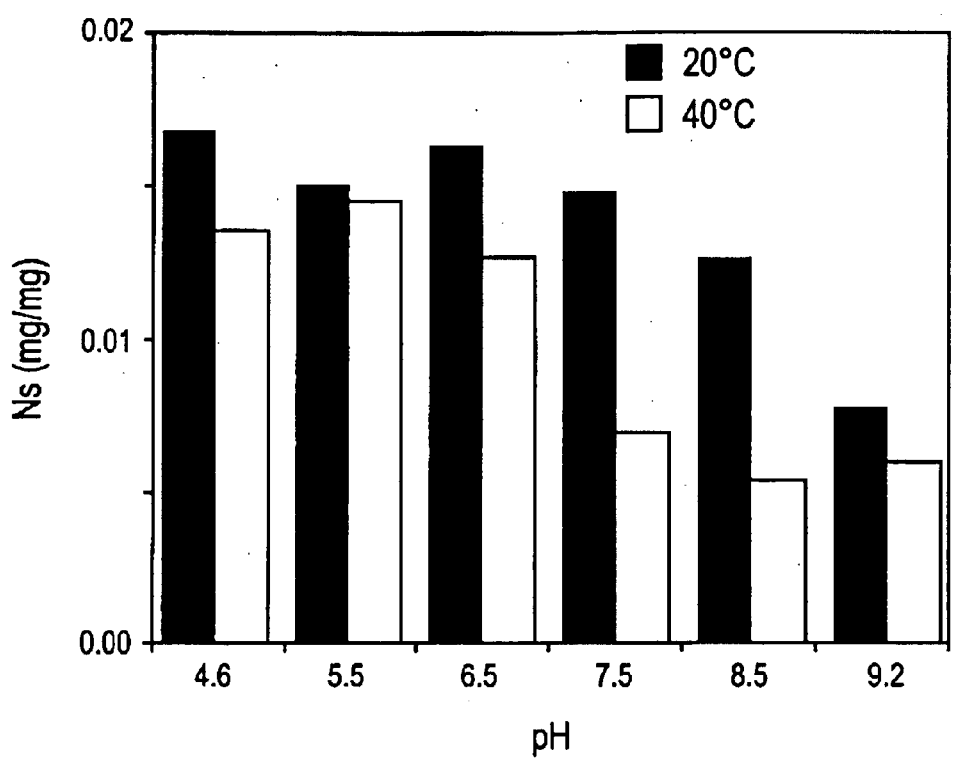
Figure 3:
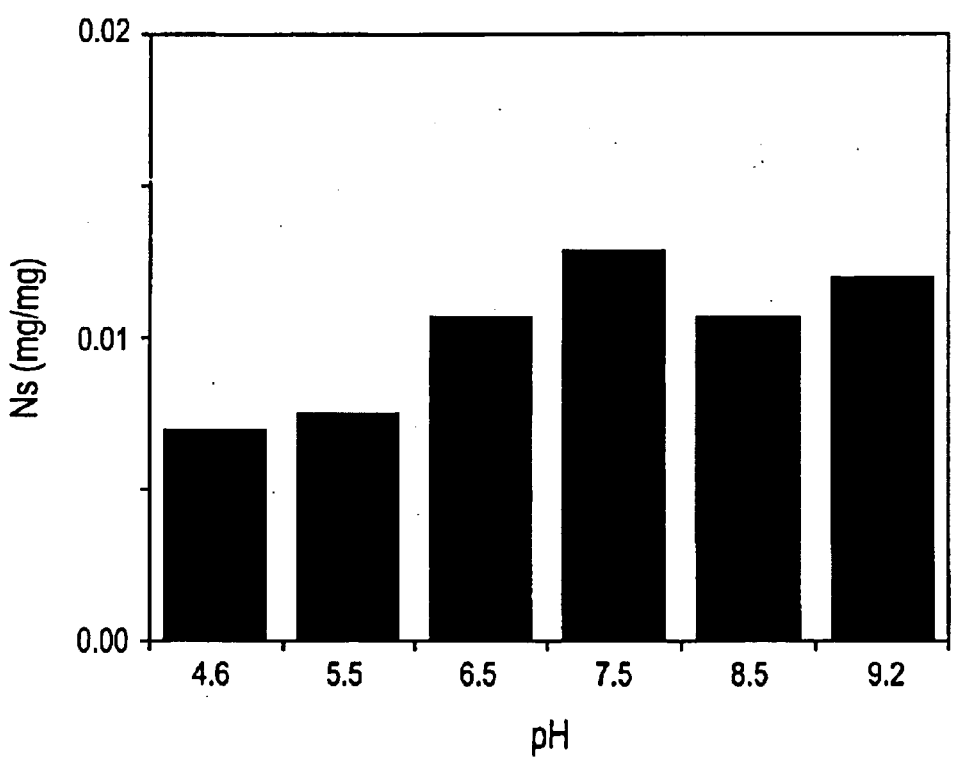
Figure 4:
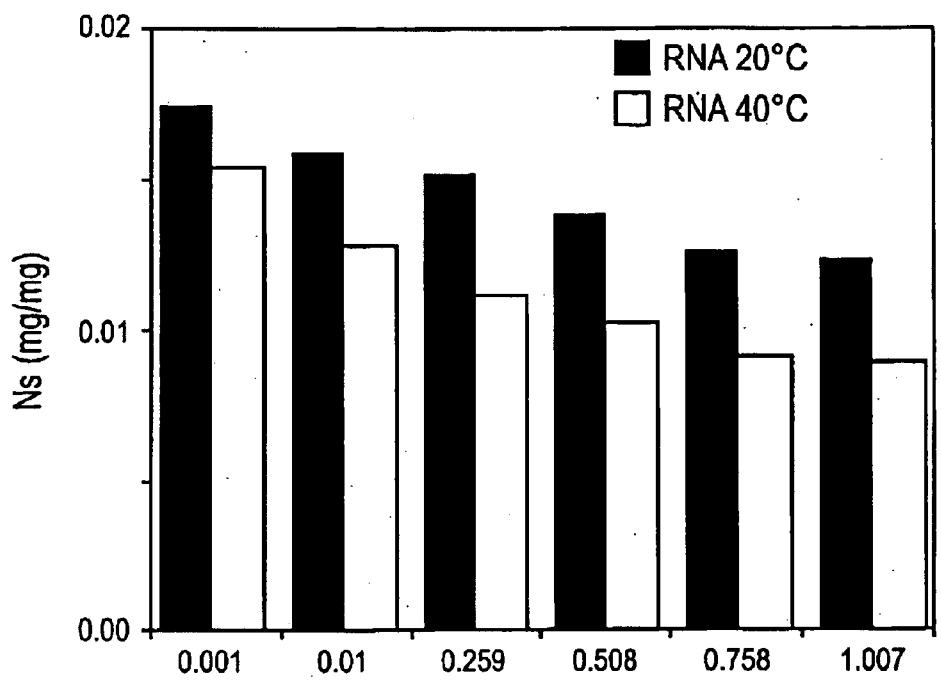
Figure 5:
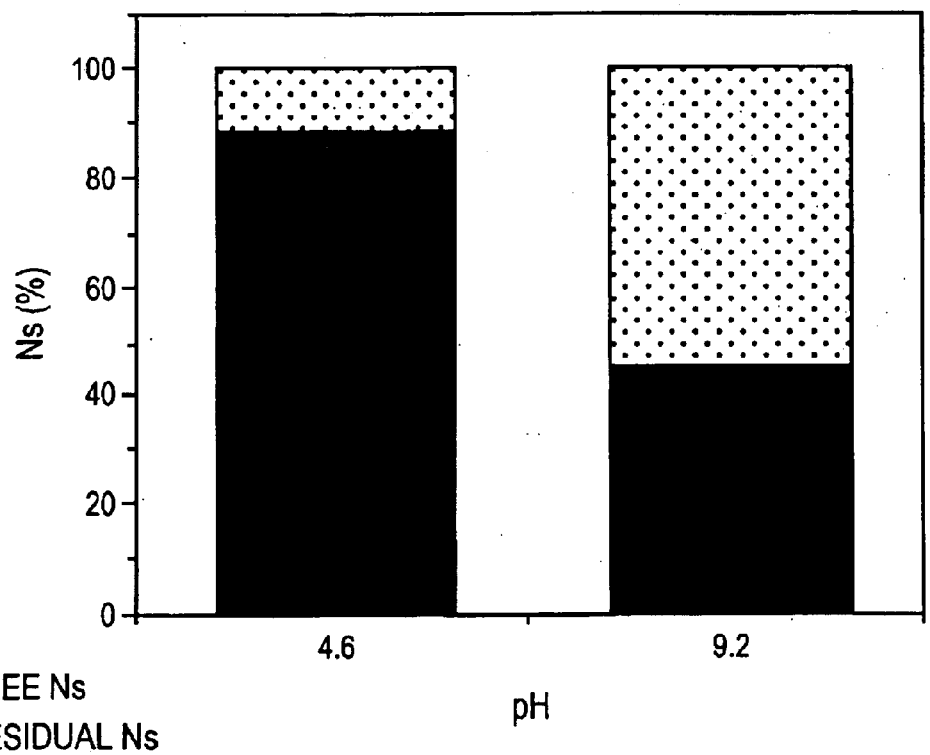
Figure 6:
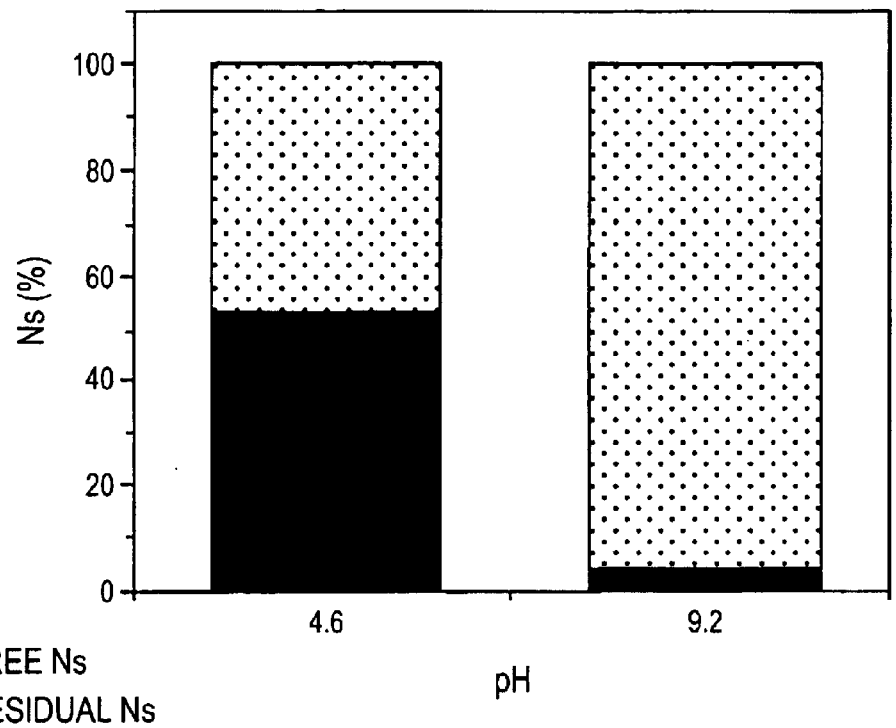
Figure 7:
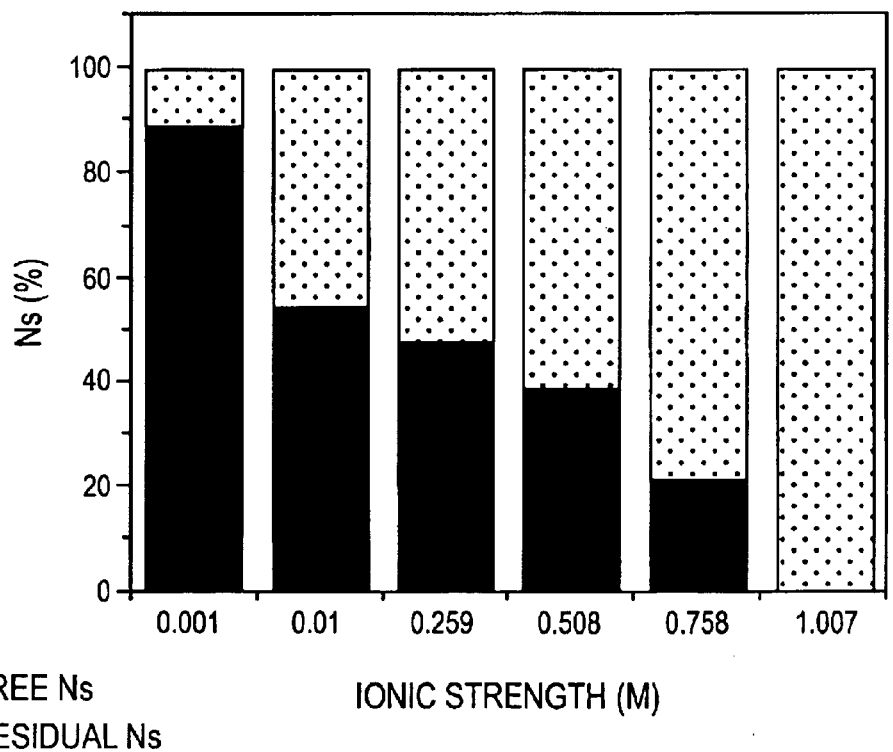

The present invention is now described with reference to Examples 1 to 6 and to FIGS. 1 to 7 which are presented below:

FIG. 1 represents the variation in the interface of the polymer as a function of the pH and the temperature, FIG. 2 represents the effect of the pH and the temperature on the adsorption of RNA, FIG. 3 represents the effect of the pH at 40° C. on the adsorption of BSA, FIG. 4 represents the effect of the ionic strength and the temperature on the adsorption of RNA, FIG. 5 represents the effect of the pH at 20° C. on the desorption of RNA, FIG. 6 represents the effect of the pH at 40° C. on the desorption of RNA, and FIG. 7 represents the effect of the ionic strength at pH 9.2 and at 20° C. upon the desorption of RNA.

For FIGS. 2 to 4, the value Ns corresponds to the quantity of the biological entity attached to the polymer and is expressed in milligrams of biological molecules attached per milligram of polymer.

For FIGS. 5 to 7, the value Ns corresponds to the percentage of liberated RNA (free Ns) or of non-liberated RNA (residual Ns), relative to the quantity of RNA previously adsorbed onto the particles in accordance with Example 2.

As the following examples will illustrate, the pH, ionic strength and/or temperature conditions during the adsorption step (c) are decisive. Indeed, as can be observed in FIG. 1, below a pH value equal to 7 and a temperature value less than the LCST of the polymer, the polymer has a charged, hydrophilic tail, whereas above a pH value equal to 7 at a temperature value greater than the LCST, the polymer exhibits a hydrophobic and neutral retracted conformation, which brings about a decrease in the adsorption of the nucleic acids and at the same time an increasing adsorption of proteins.

EXAMPLE 1

Preparation of a Nipam-based Polymer

Three polymerization techniques were used for the preparation of this polymer:

1) batch polymerization (or closed reactor process);
2) semicontinuous polymerization and 3) polymerization on a seed. In each of these techniques, the following same reagents were used:
   First monomer: N-isopropylacrylamide (NIPAM) marketed by Kodak,
   Cross-linking agent: N,N-methylenebisacrylamide (MBA) available from Aldrich,
   Initiator: 2,2'-azobisamidinopropane chloride (V50) marketed by Wako,
   Salt to adjust the ionic strength: NaCl (Prolabo),
   Functional, second monomer: 2-aminoethylmethacrylate chloride (AEM) marketed by Kodak.

1) Batch Polymerization

The first monomer (NIPAM), the functional, second monomer (AEM) and the cross-linking agent (MBA) are introduced together in a single step before the polymerization is initiated by the addition of the initiator (V50) which decomposes under the effect of heat, producing free radicals. The duration of polymerization is 30 min.

The formulation of the polymer obtained, to which the reference PNIPAM42 has been given, is the following:

| | |
|---|---|
| total volume[a] | 250 ml |
| NIPAM | 48.51 mmol |
| MBA | 3 mmol |
| AEM | 0.48 mmol |
| V50 | 0.30 mmol |
| temperature | 70° C. |

(a) Boiled and Degassed Water

The characteristic of the polymer obtained are presented in the following Table I:

TABLE I

| Diameter[a] DDL 20° C. | Diameter[b] size DDL 40° C. | Diameter[c] TEM | AEM[d] concentration | LCST[e] | CCC[f] at 20° C. |
|---|---|---|---|---|---|
| 292 nm | 164 nm | 129 nm | 14.1 μmol/g of polymer | 31.5° C. | 1.00 mol/l |

[a] diameter measured by dynamic diffusion of light at 20° C.
[b] diameter measured by dynamic diffusion of light at 40° C.
[c] diameter measured by transmission electron microscopy
[d] charge density expressed in μmol (primary amine)/g of polymer
[e] low critical solubility temperature (LCST) determined by measurement of turbidity as a function of the temperature
[f] critical concentration for coagulation (CCC) at 20° C. determined by measurement of turbidity as a function of the salinity (NaCl).

2) Semicontinuous Polymerization

A portion of the functional, second monomer is introduced into the reactor over a period between the beginning of the polymerization and the end of the total conversion thereof. This addition can be carried out at a constant speed of injection (polymerization by continuous addition) or alternatively according to a well-controlled addition at regular intervals (semicontinuous polymerization). The aim of this method of polymerization is to increase the incorporation of functional, second monomer (charged) without increasing the percentage of water-soluble polymer in the reaction medium which could disrupt the progress of the polymerization.

The formulation of the polymer obtained, to which the reference PNIPAM45 was given, is the following:

| total volume[a] | 250 ml |
|---|---|
| NIPAM | 48.51 mmol |
| MBA | 3 mmol |
| AEM | 0.48 mmol |
| V50 | 0.30 mmol |
| temperature | 70° C. |
| additions | between 3 and 6 min |

(a) boiled and degassed water

The characteristic of the polymer PNIPAM45 obtained are presented in the following Table II:

TABLE II

| Diameter[a] DDL 20° C. | Diameter[b] size DDL 40° C. | Diameter[c] TEM | AEM[d] concentration | LCST[e] | CCC[f] at 20° C. |
|---|---|---|---|---|---|
| 823 nm | 530 nm | 327 nm | 10.0 µmol/g of polymer | 32° C. | 1.00 mol/l |

[a]diameter measured by dynamic diffusion of light at 20° C.
[b]diameter measured by dynamic diffusion of light at 40° C.
[c]diameter measured by transmission electron microscopy
[d]charge density expressed in µmol (primary amine)/g of polymer
[e]low critical solubility temperature (LCST) determined by measurement of turbidity as a function of the temperature
[f]critical concentration for coagulation (CCC) at 20° C. determined by measurement of turbidity as a function of the salinity (NaCl).

3) Polymerization on a Seed

This technique consists in introducing the functional, second monomer into a reaction medium containing a previously prepared and perfectly characterized polymer. The functional, second monomer can be added alone or mixed with the monomer(s) or comonomers, in one step or semi-continuously.

The formulation of the polymer obtained, to which the reference PNIPAM94 was given, is the following:

a volume of 40 ml of seed with a solid level of 4.5% is used. The reagents were added diluted in a volume of 5 ml of water. The molar percentages of NIPAM, MBA and V50 added in the second step are identical to those of the seed (cf 1)). On the other hand, the concentration of functional second monomer is controlled (increased or decreased according to the desired charge density); in this case 10% (mol) of AEM is added relative to the first monomer NIPAM.

The characteristics of the polymer PNIPAM94, obtained after reinoculation using the seed registered under the ref erence PNIPAM93, synthesized according to the procedure described in 1), are presented in the following Table III:

TABLE III

| Diameter[a] DDL 20° C. | Diameter[b] size DDL 40° C. | Diameter[c] TEM | AEM[d] concentration | LCST[e] | CCC[f] at 20° C. |
|---|---|---|---|---|---|
| 504 nm | 290 nm | 176 nm | 22.4 µmol/g of polymer | 32° C. | 1.10 mol/l |

[a]diameter measured by dynamic diffusion of light at 20° C.
[b]diameter measured by dynamic diffusion of light at 40° C.
[c]diameter measured by transmission electron microscopy
[d]charge density expressed in µmol (primary amine)/g of polymer
[e]low critical solubility temperature (LCST) determined by measurement of turbidity as a function of the temperature
[f]critical concentration for coagulation (CCC) at 20° C. determined by measurement of turbidity as a function of the salinity (NaCl).

At the end of polymerization, the particles are collected simply by centrifugation and redispersed in water or in a desired medium.

The characteristics of the polymer obtained according to any one of techniques 1) to 3) are the following:

- charge density (cationic) between 5 and 150 µmol/g of polymer
- particle size range between 0.05 and 2 µm, particle diameter measured by dynamic diffusion of light at 20° C.
- range of critical concentration for coagulation (CCC) between 0.001 and 1.5 mol/l NaCl at 20° C. and between 0.01 and 0.9 mol/l NaCl at 40° C.

EXAMPLE 2

Adsorption of RNA or of BSA (Bovine Serum Albumin) on Particles of PNIPAN Polymer as Prepared According to Example 1

The following protocol constitutes the general procedure for the adsorption reactions:

The reaction mixture consists of 10 µl of RNA (4 mg/ml) or of 50 µl of BSA (5 mg/ml), and of 50 µl of NIPAM particles (45 g/l). The final volume of one milliliter is obtained by adding phosphate buffer (10 mM pH 4.6 or 9.2) and NaCl (5 M) so as to reach the desired ionic strength and pH.

The molecular entity (RNA or BSA) is adsorbed onto the particles over 2 hours (at 20 or 40° C.) with predetermined conditions (pH, ionic strength): the mixture is centrifuged for 20 minutes at 14,000 revolutions per minute. The supernatant is recovered, filtered on Millipore filter MILLEX-GV13 (0.22 µm) in order to remove the polymer particles in suspension. The quantity of the biological entity attached to the polymer support is determined by a simple difference between the quantity initially introduced and the remaining and free quantity (assayed in the supernatant): this quantity is expressed in milligram of biological molecules per milligram of polymer (Ns). The concentrations of RNA or of BSA are estimated by UV spectrophotometry (Kontron Instrument) at a wavelength of 260 nm or 280 nm, respectively.

The trials were carried out with E. coli 16S and 23S ribosomal RNA (Boerhinger) and BSA (Sigma reference A0281) used without prior purification.

The particles used are heat-sensitive particles of PNIPAM94. These particles are very hydrophilic at room temperature and hydrophobic at a temperature greater than the LCST (32° C.). They were synthesized as described in Example 1.

Acid phosphate (KH$_2$PO$_4$ 10 mM pH 4.6)) and basic phosphate (K$_2$HPO$_4$ 10 mM pH 9.2) buffers were used for the adsorption reactions and to control the pH of the reactions.

NaCl (5 M) was used to control the ionic strength of the reactions.

The water used in all the reactions was purified on the MILLIPOR-MILLE Q purification system.

The incubations were performed on a THERMOMIXER (Eppendorf 5436).

All the reactions were carried out in 1.5 ml Eppendorf tubes.

1) Study of the Influence of the pH and of the Temperature on the Adsorption

In accordance with FIG. 2, a better adsorption of the RNA is observed at acidic pH than at basic pH. At acidic pH, the particles are widely positively charged and the negatively charged nucleic acids attach to the particles via electrostatic forces. The attachment is greater at 20° C. than at 40° C. The results at 40° C. illustrate a decrease in the adsorption.

In accordance with FIG. 3, at 40° C., the adsorption of BSA onto the particles is possible with no influence of the pH. At 20° C., no attachment of BSA is observed because of the hydrophilic character of the particles at this temperature.

2) Study of the Influence of Ionic Strength and of the Temperature on the Adsorption In accordance with FIG. 4, the attractive electrostatic forces between the negatively charged RNAs and the positively charged polymer surface decrease with the increase in ionic strength with, as a consequence, a decrease in the attachment of the RNA.

Under the same experimental conditions, it was verified that the increase in the ionic strength does not promote the attachment of BSA onto the particles.

In conclusion, the nucleic acids are preferably adsorbed onto the particles at a temperature less than the LCST (20° C.), at a low ionic strength and at acidic pH. Under these conditions, the adsorption of the proteins (such as BSA) is not favored.

EXAMPLE 3

Desorption of RNA Adsorbed Onto Particles of PNIPAM Polymer

The reagents used are the same as those described in Example 2.

The following protocol constitutes the general procedure for the desorption reactions:

After an adsorption step performed as in Example 2, the desorption reaction is carried out after the centrifugation step at 14,000 revolutions per minute. The supernatant is removed and replaced with one milliliter of desorption buffer (phosphate (10 mM pH 4.6 or 9.2) and NaCl (5 M)) so as to obtain the desired pH and ionic strength. The desorption is performed for 2 hours at 20° C. or 40° C. The mixture is then centrifuged for 20 minutes at 14,000 revolutions per minute. The supernatant is recovered, filtered on MILLIPORE-MILLEX GV13 filter (0.22 μm) so as to remove the polymer particles in suspension. The quantity of RNA liberated is determined by UV spectrophotometry (Kontron Instrument) at a wavelength of 260 nm. The nucleic acid recovered is available for other analyses.

1) Study of the Influence of the pH and of the Temperature on the Desorption of the RNA According to FIG. 5, the desorption of the nucleic acids at the basic pH is greater because of the loss of charge on the polymer; at acidic pH, the quantity of liberated nucleic acids is much lower because the particles are then highly positively charged.

In accordance with FIG. 6, as above, the desorption of the nucleic acids is promoted at basic pH. It is also promoted by the increase in temperature because for a temperature greater than the LCST (32° C.) the particles retract.

2) Study of the Influence of the Ionic Strength on the Desorption of the RNA

In accordance with FIG. 7, as the ionic strength increases, the attractive electrostatic interactions between the RNAs and the polymer surface decrease.

In conclusion, the desorption of the nucleic acids is preferably performed at 40° C., at a high ionic strength and a basic pH.

Moreover, the retracting property of the particles at 40° C. (temperature greater than the LCST) can be exploited for concentrating a nucleic acid solution. Indeed, after adsorption of the nucleic acids and elevation of the temperature above the LCST, the particles onto which the nucleic acids are adsorbed retract, thus occupying a smaller volume than in the relaxed state and allowing the particles to be taken up, after centrifugation, in a smaller final volume.

EXAMPLE 4

Adsorption and Desorption of DNA From a Mixed DNA and BSA Solution Using the NIPAM Particles The solution of *Staphylococcus epidermidis* DNA is extracted and purified from colonies isolated from bacteria, according to the protocol described by D. Treco in Short Protocols in Molecular Biology Second Edition Ed : Harvard Medical School, 1992, pp. 2–4/2–7.

A 10% (w/v) BSA (bovine serum albumin) solution (Intergen 3210-01) in MILLIQ water is used.

PCR protocol: the PCR technique followed is that described by Goodman in PCR Strategies Ed: Innis, Gelfand and Sninsky Academic Press 1995, pp. 17–31. Two amplification primerrs were used; they have the following sequences:

Primerr 1: 5' ATCTTGACATCCTCTGACC 3'--->SEQ ID N01

Primerr 2: 5' TCGACGGCTAGCTCCAAAT 3'--->SEQ ID N02

The following temperature cycles were used during the amplification protocol:

| | | |
|---|---|---|
| once | 3 minutes | 94° C. |
| | 2 minutes | 65° C. |
| 35 times | 1 minute | 72° C. |
| | 1 minute | 94° C. |
| | 2 minutes | 65° C. |
| once | 5 minutes | 72° C. |

10 μl of amplification product are deposited on 0.8% agarose gel (FMC 50003) previously stained with ethidium bromide. After electrophoretic migration for 45 minutes at 180 V, the nucleic acid bands are visualized under ultraviolet radiation (D. Voytas in Short Protocols in Molecular Biology Second Edition Ed: Harvard Medical School, 1992, pp. 2–13/2–14).

1) Adsorption and Desorption of DNA on Particles and Detection After PCR Technique of the DNA Liberated A DNA solution ($10^{10}$ copies/ml) was adsorbed onto the particles at 20° C., pH 4.6 for two hours and then subjected to a 15 minute desorption step at 41° C., pH 8.3, ionic strength 0.05 M as described in Examples 2 and 3, respectively. After the desorption step and centrifugation, the material recovered in 50 µl of supernatant was amplified by PCR and analyzed on a 0.8% agarose gel. A band of the expected size (490 pb) is detected on the gel. Moreover, the quantity of DNA detected after PCR is at least equivalent to that detected after PCR amplification of $10^6$ copies/ml of DNA not previously adsorbed onto the particles.

The particles of NIPAM94 can therefore also be used to adsorb DNA. After desorption, the DNA can be used in a PCR-type amplification reaction.

2) Adsorption of DNA from a Mixed DNA and BSA Solution, and Detection After PCR Technique of the DNA Liberated by Desorption A DNA solution ($10^{10}$ copies/ml) in the presence of 10% (w/v) of BSA is subjected to an adsorption and desorption step as described in Example 4–1. The same amplification and detection techniques are used. A DNA of expected size (490 pb) is detected on a gel. The intensity of the DNA band visualized is the same in the presence of or in the absence of BSA.

The particles of NIPAM94 make it possible to adsorb and liberate by desorption DNA derived from a mixed DNA—10% BSA solution. The presence of BSA in the initial solution does not disrupt the adsorption of the DNA onto the particles.

EXAMPLE 5

Purification of Nucleic Acids Derived from a Bacterial Lysate (*Staphylococcus epidermidis*) Using the Particles of NIPAM 1) Preparation of the Bacterial Lysate A culture of *Staphylococcus epidermidis* is formed overnight at 37° C. The number of bacteria contained in the suspension is estimated by measuring the optic density at 550 nm. Bacterial pellets, containing respectively $2.10^6$, $2.10^4$ and $2.10^1$ bacteria, are prepared in 1.5 ml tubes by centrifugation for 3 minutes at 14,000 revolutions. The supernatant is removed and the bacterial pellet is lysed according to the technique described below (adaptation of Arora et al., J. Dairy Sci. 1990, 73, 264–273).

The pellet is taken up in 1 ml of buffer (30 mM Tris, 100 mM NaCl, 5 mM EDTA, pH 7.2) containing 6 mg/ml of proteinase K (Boehringer) and 300 µl of glass beads. This mixture is stirred on a vortex and incubated for 15 minutes at 37° C. After a centrifugation step (3 minutes at 14,000 revolutions), the supernatant containing the nucleic acids, is recovered for the subsequent stages.

2) Purification of the Nucleic Acids

The particles used are heat-sensitive particles of PNIPAM94 whose synthesis is described in Example 1.

The following protocol constitutes the general procedure for the purification reactions.

The reaction mixture consists of 50 µl of bacterial lysate, containing respectively $10^5$, $10^3$ and $10^6$ bacteria, and 2 mg of particles. The final volume of one milliliter is obtained by adjusting the reaction volume with phosphate buffer (10 mM, pH /4.6). The reaction is incubated for 30 minutes on a THERMOMIXER (Eppendorf 5436) at 20° C. After a centrifugation step of 20 minutes at 14,000 revolutions per minute, the supernatant is removed. The desorption of the nucleic acids, attached to the particles, is performed by the effect of the ionic strength by adding 50 µl of elution buffer (0.5 M KCl, pH 8.3); the reaction is incubated for 15 minutes at 42° C. on the thermomixer. After another centrifugation step of 20 minutes, at 14,000 revolutions per minute, the supernatant containing the nucleic acids is recovered; 10 µl are used for a DNA amplification step (PCR) and 5 µl for an RNA amplification step (NASBA).

3) Detection of the Nucleic Acids

The purified nucleic acids are analyzed after an enzymatic amplification step (PCR for DNA and NASSA for RNA). The amplification products are then revealed by the ELOSA (Enzyme Linked Oligo Sorbent Assay), microplate (NASBA) or VIDAS (PCR) techniques.

PCR protocol: The protocol followed is the same as that described in Example 4. The amplification products (90 µl) are analyzed on an automatic VIDAS immunoanalysis machine (bioMérieux) in accordance with the protocol described by Mabilat et al., J. Clin. Microbiol; 1994, 32, 2702–2705, the capture and detection probes being the following:

capture probe:
5' ACCACCTGTCACTCTGTCCC 3' SEQ ID NO: 3 detection probe:
5' GGAAGGGGAAAACTCTATCTC 3' SEQ ID NO: 4

The detection probe is conjugated with alkaline phosphatase.

NASBA protocol: The protocol followed is the same as that described by Kievits et al., J. Virol. Methods (1991) 35, 273–286. The primerrs used have the following sequences:

primer 1:
5' TCGAAGCAACGCGAAGAACCTTACCA 3' SEQ ID NO: 5 primerr 2:
5' AATTCTAATA CGACTCACTA TAGGGAGGTT TGTCACCGGC AGTCAACTTAGA 3' SEQ ID NO: 6

The amplification products (5 µl) are analyzed with an Elosa technique in microplate format in accordance with the protocol described by Mallet et al., J. Clin. Microbiol. (1993) 31, 1444–1449. The capture and detection probes have the following sequences:

capture probe:
5' GATAGAGTTTTCCCCTTC 3' SEQ ID NO: 7 detection probe:
5' GACATCCTCTGACCCCTCTA 3' SEQ ID NO: 8

The detection probe is conjugated with horseradish peroxidase.

Proteinase K being a known inhibitor of amplification reactions, 1/10 serial dilutions are carried out before the amplification steps in order to quantify the degree of purification obtained.

The results obtained are assembled in Table IV in the annex.

The inhibitory power of proteinase K is checked since it is necessary to dilute the sample 1/1000 before the amplification step. After the purification step, the sample is now diluted only 1/10 before the amplification step, which represents a gain of a factor of 100. The particles make it possible to purify conjointly the RNA and the DNA present in the sample. These nucleic acids are compatible with the enzymatic amplification steps.

EXAMPLE 6

Purification of Nucleic Acids Derived from a Bacterial Lysate (*Staphylococcus epidermidis*) Using the Polymer NIPAM Grafted on a Magnetic Core The particles described in the preceding examples have the disadvantage of requiring centrifugation steps after the adsorption and desorption steps. These steps are long (twice 20 minutes) and are automatible with difficulty. A possible alternative is to graft the Nipam polymer onto cationic magnetic supports. One of the supports tested is the cationic magnetic latex R95-07 (ESTAPOR, Rhône-Poulenc) whose particles are polydisperse.

The purification capacity of particles thus obtained was tested.

1) Synthesis of the Magnetic Particles of Nipam

The cationic ESTAPOR particles R95-07 were encapsulated. Before each encapsulation, the particles were washed three times with a 0.005 M hydrochloric acid solution.

1 g of seed particles is diluted in 40 ml of MILLIQ water previously heated to boiling temperature and degassed with nitrogen.

| | |
|---|---|
| Styrene: | 100 µg |
| NIPAM: | 0.3254 g |
| BAM: | 0.0274 g |
| MAE: | 0.0740 g |
| Triton X-405: | 0.14 g |
| V50: | 0.0061 g |

100 µg of styrene for the presoiling step (time 2 h at 70° C.), NIPAM, BAM and MAE are solubilized in 10 ml of water and introduced onto the seed (ESTAPOR latex). The initiator, solubilized in 1 ml of water, is added so as to allow the polymerization around the seed particles. The polymerization is performed under a nitrogen atmosphere at 70° C.

These particles then carry a charge of 220 and 82 µmol of $NH_2$/g of particles without modifying the size distribution of the particles.

2) Purification of the Nucleic Acids

The protocol used is the same as that described in Example 5 with the following modifications.

200 µg of particles were used, the centrifugation steps, to separate the particles from the supernatants, are eliminated and replaced by separation steps under the effect of a magnetic field (magnetic separation device, Promega Z5342).

All the other steps remain unchanged.

The results are assembled in Table V in the annex.

The inhibitory power of proteinase K is again observed since it is necessary to dilute the sample 1/1000 before the amplification step. After the purification step, the sample can be diluted 1/10 (PCR) or 1/100 (NASBA) before the purification step, which represents a gain of a factor of 10 to 100. These particles also make it possible to purify conjointly the RNA and the DNA present in the sample. These nucleic acids are compatible with the enzymatic amplification steps.

TABLE IV

| | | Before purification | After purification |
|---|---|---|---|
| PCR VIDAS | $10^7$ bacteria | neg° | nt* |
| | 1/10 | neg | +++ |
| | 1/100 | neg | +++ |
| | 1/1000 | +++ | +++ |
| | 1/10000 | +++ | nt |
| | $10^5$ bacteria | neg | nt |
| | 1/10 | neg | +++ |
| | 1/100 | neg | + |
| | 1/1000 | + | neg |
| | 1/10000 | neg | nt |
| | $10^0$ bacteria | neg | nt |
| | 1/10 | neg | neg |
| | 1/100 | neg | neg |
| | 1/1000 | neg | + |
| | 1/10000 | neg | nt |

TABLE IV-continued

| | | Before purification | After purification |
|---|---|---|---|
| NASBA ELOSA | $10^7$ bacteria | neg | nt |
| | 1/10 | neg | +++ |
| | 1/100 | neg | +++ |
| | 1/1000 | +++ | +++ |
| | 1/10000 | +++ | nt |
| | $10^5$ bacteria | neg | nt |
| | 1/10 | neg | neg |
| | 1/100 | neg | +++ |
| | 1/1000 | ++ | +++ |
| | 1/10000 | +++ | nt |
| | $10^0$ bacteria | neg | nt |
| | 1/10 | neg | + |
| | 1/100 | neg | +++ |
| | 1/1000 | +++ | +++ |
| | 1/10000 | +++ | nt |

°neg: negative
*nt: not tested
§RFV: relative fluorescent value
OD: optical density
VIDAS
>5000 RFV§: +++
2000–5000 RFV: ++
500–2000 RFV: +
<500 RFV: neg
ELOSA
OD# saturated: +++
OD 1000–2500: ++
OD 300–1000: +
OD <300: neg

TABLE V

| | | Before purification | After purification |
|---|---|---|---|
| PCR VIDAS | $10^7$ bacteria | neg° | nt* |
| | 1/10 | neg | +++ |
| | 1/100 | neg | ++ |
| | 1/1000 | +++ | + |
| | 1/10000 | +++ | nt |
| | $10^5$ bacteria | neg | nt |
| | 1/10 | neg | neg |
| | 1/100 | neg | neg |
| | 1/1000 | + | neg |
| | 1/10000 | neg | nt |
| | $10^0$ bacteria | neg | nt |
| | 1/10 | neg | neg |
| | 1/100 | neg | ++ |
| | 1/1000 | neg | neg |
| | 1/10000 | neg | nt |
| NASBA ELOSA | $10^7$ bacteria | neg | nt |
| | 1/10 | neg | neg |
| | 1/100 | neg | +++ |
| | 1/1000 | +++ | +++ |
| | 1/1000 | +++ | nt |
| | $10^5$ bacteria | neg | nt |
| | 1/10 | neg | neg |
| | 1/100 | neg | + |
| | 1/1000 | ++ | +++ |
| | 1/10000 | +++ | nt |
| | $10^0$ bacteria | neg | nt |
| | 1/10 | neg | neg |
| | 1/100 | neg | +++ |

TABLE V-continued

| | Before purification | After purification |
|---|---|---|
| 1/1000 | +++ | +++ |
| 1/10000 | +++ | nt |

°neg: negative
*nt: not tested
§RFV: relative fluorescent value
OD: optical density
VIDAS
>5000 RFV§: +++
2000–5000 RFV: ++
500–2000 RFV: +
<500 RFV: neg
ELOSA
OD# saturated: +++
OD 1000–2500: ++
OD 300–1000: +
OD <300: neg

What is claimed is:

1. Process for the isolation in aqueous phase of a nucleic material present in a sample by adsorption of said nucleic material onto a particulate support, comprising:
   (a) providing an adsorption reagent comprising a sol consisting of an aqueous continuous phase and a discontinuous phase of the particulate support, which comprises a functionalized, particulate polymer, said polymer being obtained by polymerization of (1) a first water-soluble monomer of acrylamide or of an acrylamide derivative, (2) at least one cross-linking agent and (3) at least a second cationic and water-soluble functional monomer, said polymer having a predetermined lower critical solubility temperature (LCST) which is between 25 and 45° C.,
   (b) bringing into contact the adsorption reagent with the sample containing the nucleic material to form a sol having an aqueous continuous phase and a discontinuous phase in which the nucleic material is adsorbed to the particulate support,
   wherein, in said contacting step (b), the sol has:
      an ionic strength at most equal to $10^{-2}$ M,
      a pH at most equal to 7, and
      a temperature less than the LCST of the polymer,
   (c) optionally observing that the adsorption has taken place, and
   (d) separating the discontinuous phase from the continuous phase.

2. Process for the isolation in aqueous phase of a nucleic material present in a sample by adsorption of said nucleic material onto a particulate support, comprising:
   (a) providing an adsorption reagent comprising a sol consisting of an aqueous continuous phase and a discontinuous phase of the particulate support, which comprises a functionalized, particulate polymer, said polymer being obtained by polymerization of (1) a first water-soluble monomer of acrylamide or of an acrylamide derivative, (2) at least one cross-linking agent, and (3) at least a second cationic and water-soluble functional monomer, said polymer having a predetermined lower critical solubility temperature (LCST) which is between 25 and 45° C.,
   (b) bringing into contact the adsorption reagent with the sample containing the nucleic material to form a sol having an aqueous continuous phase and a discontinuous phase in which the nucleic material is adsorbed to the particulate support,
   wherein, in said contacting step (b), the sol has:
      a pH at most equal to 7,
      an ionic strength at most equal to $10^{-2}$ M, and
      a temperature less than the LCST of the polymer,
   (c) optionally observing that the adsorption has taken place,
   (d) separating the discontinuous phase from the continuous phase, and
   (e) dissociating the nucleic material, by desorption, from the particulate support by increasing the ionic strength up to an ionic strength greater than $10^{-2}$ M.

3. Process according to claim 2, wherein for the desorption step (e), at least one of the parameters selected from the pH and the temperature is in addition varied as follows:
   increase in the pH up to a pH greater than 7,
   increase in the temperature up to a temperature greater than the LCST of the polymer.

4. Process according to claim 2, wherein the particulate support consists of a functionalized particulate polymer obtained by polymerization of (1) a first water-soluble monomer of acrylamide or of an acrylamide derivative, (2) at least one water-soluble cross-linking agent and (3) at least a second cationic and water-soluble functional monomer, said polymer having a predetermined lower critical solubility temperature (LCST) which is between 25 and 45° C.

5. Process according to claim 2, wherein the particulate support comprises, in addition, an organic or inorganic core, completely or partially coated with said particulate polymer, said core not modifying the adsorption properties of the polymer in relation to said nucleic material.

6. Process according to claim 5, wherein the core is a polystyrene core.

7. Process according to claim 5, wherein the core comprises a magnetic compound.

8. Process according to claim 2, wherein at least one probe and/or primer capable of specifically hybridizing to the nucleic material is added to the sample before contacting the adsorption reagent and the sample, or to the sol after contacting the adsorption reagent and the sample.

9. Process according to claim 2, wherein:
   in the contacting step (b), the adsorption reagent is brought into contact with the nucleic material, the nucleic material consisting of a primer, in order to obtain a hybridization reagent, and
   after having optionally observed that the adsorption has taken place, and separated the hybridization reagent from the sol, said hybridization reagent is brought into contact with a medium containing at least one nucleic acid or nucleic acid fragment, under suitable conditions for the hybridization or the extension of the primer.

10. Process according to claim 2, wherein the LCST of the polymer is between 30 and 40° C.

11. Process according to claim 2, wherein the first monomer (1) is selected from N-alkylacrylamides and N,N-dialkylacrylamides.

12. Process according to claim 11, wherein the first monomer (1) is selected from the group consisting of N-isopropylacrylamide, N-ethylmethacrylamide, N-n-propylacrylamide, N-n-propylmethacrylamide, N-isopropylmethacrylamide, N-cyclopropylacrylamide, N,N-diethyl acrylamide, N-methyl-N-isopropylacrylamide, and N-methyl-N-n-propylacrylamide.

13. Process according to claim 2, wherein the second functional monomer(s) (3) are selected from the group consisting of cationic acrylic and methacrylic derivatives, 2-aminoethylmethacrylate chloride (AEM), N-vinylpyridine derivatives, trialkylammonium derivatives and isothiouronium chloride derivatives.

14. Process according to claim 2, wherein the cross-linking agent (2) is N,N-methylenebisacrylamide (MBA) or ethylene glycol dimethacrylate.

15. Process according to claim 2, wherein the polymer is obtained in the presence of a polymerization initiator selected from water-soluble neutral and cationic initiators.

16. Process according to claim 1, wherein it comprises, after the separation step (d), a desorption step according to which the nucleic material is dissociated, by desorption, from the particulate support by varying at least one of the parameters selected from the group consisting of ionic strength, pH and temperature, as follows:

increase in the ionic strength up to an ionic strength greater than $10^{-2}$ M, increase in the pH up to a pH greater than 7, increase in the temperature up to a temperature greater than the LCST of the polymer.

17. Process according to claim 2, wherein the separation step (d) is performed by a technique selected from the group consisting of centrifugation, filtration, precipitation, sedimentation, and the application of a magnetic field.

18. Process according to claim 12, wherein the first monomer is N-isopropylacrylamide (NIPAM).

19. Process according to claim 15, wherein the polymerization initiator is 2,2'-azobisamidinopropane chloride (V50).

20. Process according to claim 2, wherein, for the desorption step (e), the temperature is in addition varied to a temperature greater than the LCST of the polymer.

21. Process according to claim 16, wherein, for the desorption step, the temperature is varied to a temperature greater than the LCST of the polymer.

22. Process according to claim 4, wherein the LCST of the polymer is between 30 and 40° C.

* * * * *